United States Patent
Morrison et al.

(10) Patent No.: US 11,406,575 B2
(45) Date of Patent: Aug. 9, 2022

(54) WATER-FREE/ANHYDROUS CREAM SHAMPOO

(71) Applicant: Henkel IP & Holding GmbH, Düsseldorf (DE)

(72) Inventors: Schavel Morrison, Darien, CT (US); Marina Azizova, Darien, CT (US); Lisa Argus, Darien, CT (US)

(73) Assignee: Henkel IP & Holding GmbH

( * ) Notice: Subject to any disclaimer, the term of this patent is extended or adjusted under 35 U.S.C. 154(b) by 0 days.

(21) Appl. No.: 16/891,333

(22) Filed: Jun. 3, 2020

(65) Prior Publication Data

US 2021/0378925 A1    Dec. 9, 2021

(51) Int. Cl.
| | |
|---|---|
| A61K 8/34 | (2006.01) |
| A61K 8/362 | (2006.01) |
| A61K 8/46 | (2006.01) |
| A61K 8/73 | (2006.01) |
| A61Q 5/02 | (2006.01) |

(52) U.S. Cl.
CPC .............. *A61K 8/345* (2013.01); *A61K 8/362* (2013.01); *A61K 8/466* (2013.01); *A61K 8/737* (2013.01); *A61Q 5/02* (2013.01); *A61K 2800/31* (2013.01); *A61K 2800/596* (2013.01)

(58) Field of Classification Search
CPC ................ A61K 8/466; A61K 2800/31; A61K 2800/596; A61Q 5/02
See application file for complete search history.

(56) References Cited

U.S. PATENT DOCUMENTS

| | | | |
|---|---|---|---|
| 5,254,334 A | 10/1993 | Ramirez et al. | |
| 5,409,706 A | 4/1995 | Ramirez et al. | |
| 2013/0336903 A1* | 12/2013 | Fernandez Prieto | ... A61P 31/10 424/59 |
| 2018/0110704 A1* | 4/2018 | Zhao | ......................... A61K 8/70 |
| 2018/0110714 A1* | 4/2018 | Glenn, Jr. | ................. A61K 8/27 |
| 2018/0193231 A1* | 7/2018 | Jung | ......................... A61K 8/19 |
| 2019/0110970 A1* | 4/2019 | Erkens | .................. A61K 8/416 |

FOREIGN PATENT DOCUMENTS

| | | |
|---|---|---|
| CA | 1290689 C | 10/1991 |
| CN | 86105298 A | 6/1987 |
| EP | 0569773 A2 | 11/1993 |
| ES | 2361555 T3 | 9/2017 |
| GB | 2552566 A | 1/2018 |
| GB | 2587885 A | 4/2021 |

OTHER PUBLICATIONS

AlQuadeib, B.T. et al. "Pharmaceutical evaluation of different shampoo brands in local Saudi market" Saudi Pharmaceutical Journal 26 (2018) 98-106 (Year: 2018).*
"Smooth-on" https://www.smooth-on.com/assets/pdf/Viscosity_Scale_Reference_Guide.pdf, accessed Jul. 6, 2021, p. 1 (Year: 2021).*
Cornwell, P. A. "A review of shampoo surfactant technology: consumer benefits, raw materials and recent developments." International journal of cosmetic science 40.1 (2018): 16-30.
Anonymous: "innospec formulations", Internet Citation, [Online], May 1, 2014 (May 1, 2014), pp. 1-24, Retrieved from the Internet: URL:https://www.ulprospector.com/documents/1273346.pdf?bs=3904&b=376525&st=20> [retrieved on Feb. 23, 2017].
Examination Report for EP Application No. 21 177 556.4-1112 dated Nov. 22, 2021.
European Search Report for EP Application No. 21177556.4-1112 dated Nov. 9, 2021.
Gough; "Formulating High Performance, Sulfate-Free Cleansing Products Content"; Apr. 16, 2015 (Apr. 16, 2015), Retrieved from the Internet: URL:https://www.in-cosmetics.com/RXUK/RXUKInCosmetics/2015-Website/Documents/in-cosl5,IS,T3,D3,Formulating%20high%20performance,%20sulfate-free%20cleansing%20products,Dr.%20Tony%20Gough.pdf?v=635653985524043037 [retrieved on Jul. 19, 2019].
European Patent Office, European Search Report, EP 21 17 7556, dated Nov. 9, 2021, pp. 1-4, European Patent Office, Munich, Germany.
Dr Tony Gough, Formulating High Performance, Sulfate-Free Cleansing Products, in-cosmetics, Apr. 14-16, 2015, pp. (slides) 1-43, innospec, Gran Via Barcelona, Spain Retrieved from the Internet: https://dokumen.tips/documents/formulating-high-performance-sulfate-free-cleansing-products.html, Retrieved Feb. 16, 2022.
Anonymous: "innospec", May 2014 (May 1, 2014), p. 24PP, XP002767563, Retrieved from the Internet <URL: https://www.ulprospector.com/documents/1273346.pdf?bs=3904&b=376525&st=20> [retrieved on Feb. 23, 2017].

* cited by examiner

*Primary Examiner* — Andrew S Rosenthal
(74) *Attorney, Agent, or Firm* — St. Onge Steward Johnston & Reens LLC

(57) ABSTRACT

An anhydrous shampoo composition includes two surfactants selected from (a) sodium cocoyl isethionate, and (b) at least one of sodium lauroyl methyl isethionate and sodium cocoyl methyl isethionate; and propanediol. The compositions can further include glycerin, gaur and citric acid. The shampoos compositions are capable of foaming when combined with water during use for cleaning and conditioning keratinous fibers.

20 Claims, No Drawings

WATER-FREE/ANHYDROUS CREAM SHAMPOO

FIELD OF THE INVENTION

The present invention relates to anhydrous (water-free) cosmetic cleaning compositions that are capable of foaming when combined with water. The compositions are useful as shampoos to clean and condition keratinous fibers, in particular human hair.

BACKGROUND OF THE INVENTION

Hair shampoos are an important cosmetic commodity in many communities around the world. The properties of shampoo depend upon the intended application, but common properties include the ability to cleanse the hair, removal of excess natural oils from the scalp and the formation of foam necessary for the removal of dirt particles. Consumers consider foaming ability an important aesthetic consideration in assessing the acceptability of a shampoo.

Shampoos may be formulated as liquids, creams, pastes or dry formulations. The principal constituents in most shampoos are detergents, thickeners, foam stabilizers and boosters, perfumes, preservatives, diluents or bulking agents (usually water), conditioning agents or emollients, pearlizers/opacifiers and colorants. Bulking agents are used primarily for commercial purposes as they allow a consumer to achieve a desirable level of lathering upon dispensing a certain amount of shampoo.

Water commonly makes over 50% of shampoo formulations largely due to its property as an inert solvent and low cost. However, there are instances where it is undesirable to include water in shampoo. The use of water in a shampoo composition will typically require formulation with preservative ingredients in the product to prevent bacterial growth. Water also increases the weight and volume of the compositions, requiring larger packaging, use of non-biodegradable plastic bottles, and higher shipping costs.

Consumers and manufacturers are developing greater concerns for the planet and prefer to use products that benefits the environment by selecting energy efficient products that are biodegradable, and/or incorporate naturally derived ingredients, and/or have fewer additives or preservatives. Further, a transparent and safe product ingredient listing is an important factor in many consumer purchasing decisions. These consumer preference trends apply in the fields of skin care, hair care, and cosmetics, as shampoos are used daily.

Accordingly, there is a need in the consumer market for anhydrous non-aqueous compositions that are biodegradable, can be sold without plastic bottles, incorporate naturally derived ingredients, and/or have fewer additives or preservatives, which provide desirable foaming properties and conditioning when combined with water in use.

An anhydrous composition for skin care applications comprised of petrolatum, mineral oil and detergents is disclosed in Canadian Patent No. 1,290,689 to Vishnupad et al. However, an anhydrous hair shampoo that incorporates high levels of oil would require high levels of detergents to overcome the foam suppressing properties of the oil in the formulation. Detergents are harsh on both the consumer's hair and on the environment and a high level detergent component is undesirable. Further, the mineral oil can also cause separation of components. The petrolatum can have small cell foam properties that are better suited for skin formulations.

Similarly, European Patent Application 93,106,805 to Vishnupad et al. discloses an anhydrous composition for skin care comprised of high levels of glycerin and emollients (e.g., petrolatum or micro crystalline wax) in combination with detergent additives. The presence of emollients (e.g., petrolatum or micro crystalline wax) results in a composition that has small cell foam properties better suited for skincare products, not shampoo. Furthermore, micro crystalline wax is not a suitable ingredient for a hair care product, and it adds costs to the production of the composition and reduces foamability.

Therefore, it is an object of the present invention to provide a sustainable anhydrous cleaning composition that requires minimal ingredients, is free of harsh ingredients, and has foaming properties desirable for hair care.

It is an object of the invention to provide a cream shampoo composition that is free of water and has cosmetically acceptable texture and consistency with no separation of ingredients.

It is an object of the invention to provide a non-powder (i.e., not "dry" shampoo) sustainable shampoo composition having no added water and that is free of added preservatives. The cream form of such composition can be easily mixed with water during use.

SUMMARY OF THE INVENTION

These and other objects are achieved by providing cosmetic cleaning compositions comprising propanediol and two surfactants selected from (a) sodium cocoyl isethionate (SCI) and (b) sodium lauroyl methyl isethionate (SLMI) or sodium cocoyl methyl isethionate (SCMI). The compositions are particularly suitable as a shampoo composition that foams when subsequently combined with water in use.

In some embodiments, the shampoo composition comprises 25-50% w/w propanediol. In some of those embodiments, the composition comprises 30-50% w/w propanediol.

In certain embodiments, the shampoo composition comprises 10-45% w/w of the surfactants. In certain of those embodiments, the composition comprises 10-25% w/w of the surfactants. In some of those embodiments, the composition comprises 20-45% w/w of the surfactants.

In some preferred embodiments, the ratio of surfactants (a) to (b) is about 1:1.

In certain preferred embodiments, the ratio of the surfactants to propanediol is about 1.2:1.

In some embodiments, the shampoo composition further comprises glycerin. In certain of those embodiments, the glycerin is present at 30-50% w/w of the composition.

In certain embodiments, the shampoo composition further comprises about 0.2% w/w citric acid.

In some embodiments, the shampoo composition further comprises at least one of fragrance, conditioning agent, preservative, gums, buffering agent, and emollient.

In certain embodiments, the shampoo composition further comprises guar polymer.

In certain preferred embodiments, the shampoo is a cream.

In some embodiments, the viscosity of the shampoo is 1,000,000 cps-2,000,000 cps.

In another aspect, the invention provides a cosmetic cleaning composition that is substantially free of water comprising 30-50% w/w propanediol and 10-45% w/w surfactants selected from sodium cocoyl isethionate and at least one of one of sodium lauroyl methyl isethionate and sodium cocoyl methyl isethionate.

In some embodiments, the cosmetic cleaning composition surfactants are selected from sodium cocoyl isethionate and sodium lauroyl methyl isethionate.

In certain embodiments, the cosmetic cleaning composition further comprises glycerin. In some of those embodiments, the glycerin is present at 25-50% by weight of the composition.

In yet another aspect is provided a cosmetic cleaning composition free of added water comprising 25-50% w/w propanediol, 10-25% w/w sodium cocoyl isethionate, 10-20% w/w at least one of one of sodium lauroyl methyl isethionate and sodium cocoyl methyl isethionate, and 25-50% w/w glycerin.

In certain embodiments, the cosmetic and shampoo compositions further comprise 0.2-0.4% w/w guar polymer and about 0.17-0.2% w/w citric acid.

The present invention addresses the need for a highly sustainable hair care shampoo formula that is water free. Water free hair care shampoos are not prevalent, but they are desirable as they are better for the environment, more effective, and have a desirable consistency, making the shampoo easy to use and enabling the shampoo to be packaged and stored in a variety of ways (e.g., bottle, tube, aluminum jar, etc.).

The present invention achieves the need for an anhydrous shampoo with few ingredients due to its incorporation of propanediol. Because propanediol is a natural preservative, the present invention can limit the number of ingredients by excluding additional preservative ingredients.

The present invention also addresses consumers' desire for a shampoo that is high foaming and conditioning without including harsh ingredients and/or a multitude of ingredients.

Lastly, the present invention not only provides the above benefits, but it also is effective for the purposes for which it is intended, which is to leave a consumer who uses the product with hair that is clean, conditioned, and provided with a soft texture.

DETAILED DESCRIPTION OF THE INVENTION

The following detailed description is merely exemplary in nature and is not intended to limit the disclosure or the application and uses of the subject matter as described herein. Furthermore, there is no intention to be bound by any theory presented in the preceding background or the following detailed description.

Anhydrous typically refers to a substance that contains no water. As used herein, "anhydrous" refers to compositions in which no water has been added in during the formulation process or that are "free of added water" or that do not include free water.

"Free water" in the context of the present application is water that is not present in the form of water of crystallization, water of hydration or similar molecularly bound water in the antiperspirant composition. The content of water of crystallization, water of hydration or similar molecularly bound water which is present in the constituents used does not constitute free water in the context of the present application. Free water is, for example, water which is added to the composition as contemplated herein as a solvent or as a solvent constituent of other active substances.

As used herein, "shampoo" refers to a cleansing composition for keratinous fibres, particularly human hair.

As used herein, the term "surfactant", includes compounds that may lower the surface tension, or interfacial tension, between two liquids or between a liquid and a solid. Surfactants may act as detergents, wetting agents, emulsifiers, foaming agents, and dispersants.

It has been found that hair care shampoos having excellent cleaning and care effects can be provided by replacing the aqueous bulking agent of conventional shampoos with a non-aqueous bulking agent (i.e., the combination of propanediol, SCI, and SLMI or SCMI). This produces foamable non-aqueous compositions with foaming characteristics suitable for use as a shampoo.

Specifically, the combination of propanediol, SCI and SLMI or SOW produces a structured cream that does not require the addition of water or additional thickening/structuring agents. When combined with water by the consumer, the present invention provides a high foaming cleaning product that leaves hair clean, soft and manageable. The high foaming cleaning composition of the present invention is not achievable with emollients such as mineral oil, isopropyl myristate, propylene glycol, isododecane and oils disclosed in the prior art.

The cosmetic foamable non-aqueous compositions of the invention have the foaming properties expected by consumers of shampoos.

The foamability properties of a product can be determined by visual inspection of foaming during use. Alternatively, the cylinder shake test method can be used to determine foaming qualities. In the cylinder shake test method, diluted shampoo solution is placed in a graduated cylinder, the cylinder is sealed, and then rotated a number of times to create the foam. The test can be used to measure flash foam, foam volume and drainage time. Another foamability test is a blender foam volume/drainage test. In this test, 4 g of a 10% solution of shampoo is added to 146 g of water (50 ppm hardness) at 29° C. The solution is agitated for 10 seconds at a medium speed in a blender. The foam is poured into a 1000-mL graduated cylinder and the volume measured. After 3.5 min, the position of the foam-water interface is recorded. This gives a measure of foam drainage. A test of flash foam can be made by the same test protocol, with the agitation time decreased to 5 seconds.

The compositions of the present invention will preferably use anhydrous grade cosmetic ingredients when available, meaning that the supplier has taken steps to remove the water of crystallization.

In preferred embodiments, the compositions include no free water.

The compositions contemplated herein may also be substantially anhydrous. "Substantially anhydrous" means, as contemplated herein, a content of free water of not more than about 7% by weight, more preferably a content of free water of not more than about 4% by weight. In certain embodiments a substantially anhydrous composition will have a content of free water of not more than about 2% by weight, more preferably a content of free water of not more than about 1% by weight. The amount of free water in a substantially anhydrous composition is based on the weight of the free water as compared to the total weight of the composition.

The compositions contemplated herein require propanediol, and a specific combination of two surfactants, in particular, (a) sodium cocoyl isethionate ("SCI") (e.g., Pureact® I-85 and I-78), and (b) at least one of sodium lauroyl methyl isethionate ("SLMI") (e.g., Iselux® LQ-CLR-SB) or sodium cocoyl methyl isethionate ("SCMI").

The compositions can include additional surfactants. In addition to the aforementioned, the additional surfactants may include one or more of the following, alone, or in combination with those listed, or other surfactants or surfactant-like compounds: sodium methyl cocoyl taurate (Pureact WS Conc.); Aqua (and) Sodium Lauroyl Methyl Isethionate (and) Cocamidopropyl Betaine (and) Sodium Methyl Oleoyl Taurate (Iselux® SFS-SB), cocamidopropyl betaine (ColaTeric COAG), polyethylene sorbitol ester (e.g., Tween 80), ethoxylated lauryl alcohol (RhodaSurf 6 NAT), sodium laureth sulfate/lauryl glucoside/cocamidopropyl betaine (Plantapon 611 L UP), sodium laureth sulfate (e.g.; RhodaPex ESB 70 NAT), alkyl polyglucoside (e.g., Plantaren 2000 N UP), sodium laureth sulfate (Plantaren 200), Dr. Bronner's Castile soap, Dr. Bronner's baby soap, Lauramine oxide (ColaLux Lo); sodium dodecyl sulfate (SDS), polysulfonate alkyl polyglucoside (PolySufanate 160 P), sodium lauryl sulfate (Stepanol-WA Extra K, Sodium Laurylglucosides Hydroxypropylsulfonate (Suga® nate 160NC), lauramidopropyl betaine (Cola® Teric LMB); Cocamidopropyl hydroxysultaine (Cola® Teric CBS); disodium cocoamphodiacetate (Cola® Teric CDCX-LV); sodium laurylglucosides hydroxypropyl phosphate (Suga® Fax D12), and combinations thereof.

The amount of surfactant can range from 10 to 50% by weight of the composition, more preferably 10-45% by weight, most preferably 10-25% by weight or 20-45% by weight of the composition.

In some preferred embodiments, the amount of surfactant can range from 10.5-45% by weight of the composition, more preferably 10.5-27.5% by weight, 10.5-25% by weight, or 15-17.5% by weight of the composition. In certain preferred embodiments; the amount of surfactant can range from 12.5-45% by weight, 12.5-32.5% by weight, 12.5-30% by weight, 12.5-25% by weight, or 12.5-15% by weight of the composition.

In certain especially preferred embodiments, the surfactants consist of 10.5-20% by weight of the composition, more preferably 15-17.5% by weight of SLMI; and 12.5-25% by weight, more preferably 12.5-15% by weight, of SCI.

In other especially preferred embodiments, the surfactants consist of 10.5-20% by weight of the composition, more preferably 15-17.5% by weight, of SCMI; and 12.5-25% by weight, more preferably 12.5-15% by weight, of SCI.

In particularly preferred compositions, the ratio of SCI to (SLMI and/or SCMI) is in the range of 0.625:1 to 2.38:1. In certain preferred embodiments, the ratio of SCI to (SLMI or SCMI) is 0.625:1. In other preferred embodiments, the ratio of SCI to (SLMI or SCMI) is 1:1.

It was observed by the inventors that SLMI has a greater effect on viscosity than SCI. An increase in the percentage of SLMI significantly increases the viscosity of the shampoo compositions.

The surfactants are dissolved in the propanediol, such as 1,3-propanediol. A preferred commercially available product is ZEMEA propanediol supplied by DuPont Tate & Lyle Bo Products.

The amount of propanediol can vary but is generally in the range of 5-50% by weight of the composition, preferably 8-50% by weight, most preferably, 25-50% by weight of the composition. In some embodiments, the propanediol is about 8-25% by weight of the composition. In certain embodiments, the amount of propanediol is around 15% by weight of the composition.

In one preferred embodiment, the composition is formulated as a cream comprising surfactant dissolved in propanediol.

In certain embodiments, the ratio of surfactant to propanediol is in the range of 0.76:1 to 3.75:1. In some embodiments, the ratio of surfactant to propanediol is 3.75:1. In other embodiments, the ratio of surfactant to propanediol is 2:1. In certain preferred embodiments, the ratio of surfactant to propanediol is 1.2:1.

The compositions preferably additionally contain glycerin in combination with the surfactants and propanediol. Glycerin provides the composition with a creamy or butter consistency with good viscosity and flowability. Use of other solvents will cause the compositions to separate, have poor consistency, undesirable foam and/or oily residue.

The amount of glycerin needed to obtain a preferred embodiment of the composition of the invention is in the range of 25-55% weight of the composition, more preferably 40-55% by weight, most preferably 40-50% by weight of the composition.

In certain preferred embodiments, the amount of ingredients in an anhydrous shampoo composition includes:
  A. Surfactants 10-20% w/w
  B. Propanediol 30-50% w/w
  C. Glycerin 30-50% w/w.
The surfactants include SCI and at least one of SLMI or SCMI.

In other preferred embodiments, the amount of ingredients in an anhydrous shampoo composition includes:
  A. Surfactants 10.5-45% w/w
  B. Propanediol 25-50% w/w
  C. Glycerin 25-50% w/w
The surfactants include SCI and at least one of SLMI or SCMI.

In yet other embodiments, the amount of essential ingredients in an anhydrous shampoo composition includes:
  a. SCI 12.5-25%
  b. SLMI or SCMI 10.5-20% w/w
  c. Propanediol 25-50% w/w
In certain of those embodiments, the composition includes 25-50% w/w Glycerin.

An additional component of compositions as contemplated herein is a cationic guar polymer. Suitable cationic guar polymers are available from natural sources and give the hair a soft feel. They furthermore support the separation of the oils on the hair without negatively influencing the hair volume in the care active substance mixture of the hair cleaning agents as contemplated herein.

In the context of the present disclosure, suitable cationic guar polymers are understood to mean physiologically compatible cationic guar derivatives and/or hydrophobically modified cationic guar derivatives.

Preference is given to cationic hydroxy ($C_1$-$C_4$) alkyl guar derivatives, preferably cationic hydroxyethyltrimethylammonium guar and/or cationic hydroxypropyltrimethylammonium guar having average molecular weights (weight average) from about 100,000 to about 2,000,000 daltons; preferably from about 200;000 to about 1;750,000 daltons and in particular from about 300,000 to about 1,600,000 daltons. Further preferred are cationic hydroxy ($C_1$-$C_4$) alkyl guar derivatives, preferably cationic hydroxyethyltrimethylammonium guar and/or cationic hydroxypropyltrimethylammonium guar, having cationic charge densities of at least about 0.5 meq/g.

Especially preferred are the cationic guar polymers known under the INCI name Guar Hydroxypropyltrimonium Chloride having a molecular weight (weight average)

from about 100,000 to about 2,000,000 daltons, preferably from about 200,000 to about 1,750,000 daltons and in particular from about 300,000 to about 1,600,000 daltons and a cationic charge density of at least about 0.5 meq/g.

Suitable cationic guar polymers are available; for example; under the trade names "Jaguar®" or "N-Hance®" from different suppliers.

Particularly suitable cationic guar polymers are: Jaguar® C13S, Jaguar® C 162, Jaguar® C14S, Jaguar® C17, Jaguar® Excel, N-Hance® 3196 and/or N-Hance® 3215.

The compositions as contemplated herein contain the cationic guar polymer(s) preferably in an amount of about 0.01 to about 1.00% by weight of the composition, more preferably from about 0.02 to about 0.90% by weight, particularly preferably from about 0.2 to about 0.4% by weight, most preferably about 0.2% by weight, wherein the quantities refer to the total weight of the composition.

In order to further increase the nourishment and/or rheological properties of the agents as contemplated herein it can be advantageous if they also contain at least one cosmetic oil. Suitable cosmetic oils in the sense of the present disclosure are understood to mean oil bodies that have a melting point below about 50° C., particularly preferably below about 47° C., very particularly preferably below about 44° C., most preferably below about 40° C. Most preferred are cosmetic oils which are flowable at a temperature below about 40° C.

Preferred cosmetic oils are natural vegetable oils. Vegetable oils (and/or butters)—even when used at low concentrations—can further increase the aforementioned conditioning advantages on the hair in combination with the active substance combination a), b), c), without a buildup effect occurring with regular use. In addition, vegetable oils (and/or butters) in the nourishing active substance mixture of the hair treatment agents as contemplated herein also contribute to the improvement in hair shine.

Examples of natural vegetable oil suitable as contemplated herein are, for example, amaranth seed oil, apricot kernel oil, argan oil, avocado oil, babassu oil, cottonseed oil, borage seed oil, camelina oil, canola oil, cranberry oil, safflower oil, peanut oil, pomegranate seed oil, grapefruit seed oil, hempseed oil, rose hip oil, hazelnut oil, elderberry seed oil, blackcurrant seed oil, jojoba oil, cocoa butter, coconut oil, pumpkin seed oil, linseed oil, macadamia nut oil, corn oil, mallow oil, almond oil, mango stone oil, marula oil, poppy seed oil, evening primrose oil, olive oil, palm oil, palm seed oil, peach stone oil, rambutan oil, rapeseed oil, rice bran oil, castor oil, Sacha Inchi oil, safflower oil, seabuckthorn berry oil, seabuckthorn kernel oil, sasanqua oil, sesame oil, Shea butter, soybean oil, sunflower oil, teatree oil, grape seed oil, tsubaki oil, walnut oil, wheatgerm oil, lady's smock oil and/or wild rose oil.

Preferred are amaranth seed oil, apricot kernel oil, argan oil, avocado oil, coconut oil, almond oil, macadamia nut oil, rose hip oil, sunflower oil, olive oil, peach kernel oil, jojoba oil and/or the vegetable butters Shea butter and/or cocoa butter.

The teaching as contemplated herein also comprises the fact that at least two natural vegetable oils can be mixed with one another. Preferred mixtures of natural oils can be, for example: amaranth seed oil with seabuckthorn oil, amaranth seed oil with Shea butter, amaranth seed oil with camelina oil, amaranth seed oil with olive oil, amaranth seed oil with macadamia nut oil, olive oil with seabuckthorn oil, olive oil with camelina oil, olive oil with Shea butter, macadamia nut oil with seabuckthorn oil and/or macadamia nut oil with Shea butter.

In a preferred embodiment the hair treatment agents as contemplated herein contain a mixture of natural, vegetable oils, preferably a mixture of vegetable oils and/or vegetable butters, and in particular a mixture of coconut oil with sunflower and meadowfoam seed oil.

The one or more vegetable oil(s) (and/or butter(s)) is (are) used in the hair treatment compositions as contemplated preferably in an amount from about 0 to about 3.00% by weight, more preferably from about 0.01 to about 2.50% by weight of the composition, particularly preferably from about 0.05 to about 2.00% by weight of the composition.

In a further preferred embodiment, the cleaning compositions as contemplated herein are substantially free from silicones, and/or mineral oils. The term "substantially free" is understood to mean that the compositions as contemplated herein preferably contain less than about 0.25% by weight of, more preferably less than about 0.10% by weight of, and in particular no silicones and/or mineral oils (in relation to the total weight of the hair cleansing agents). The aforementioned amounts apply here both for freely added silicone and/or mineral oil and for silicones and/or mineral oils which might be contained in trade products as by-product.

In a further preferred embodiment, the shampoo compositions as contemplated herein are substantially free from polymeric thickeners of synthetic and/or natural origin. The term "substantially free" is understood to mean that the hair treatment agents as contemplated herein preferably contain less than about 0.25% by weight of, more preferably less than about 0.10% by weight of, and in particular no polymeric thickeners of synthetic and/or natural origin (in relation to the total weight of the hair cleansing agents). The aforementioned amounts apply here both for freely added polymeric thickeners of synthetic and/or natural origin and for polymeric thickeners of synthetic and/or natural origin which might be contained in trade products as by-product.

Further active substances, auxiliaries and additives which can preferably be present in the hair cleaning and care agents as contemplated herein are, for example: plant extracts, humectants, perfumes, UV filters, structurants such as maleic acid, dimethyl isosorbide, cyclodextrins, fiber-structure-improving active substances, in particular mono-, di- and oligosaccharides such as, for example, glucose, galactose, fructose, fruit sugar and lactose, dyes for staining the agent, active substances such as bisabolol and/or allantoin, complexing agents such as EDTA, NTA, beta-alanine diacetic acid and phosphonic acids, ceramides (Ceramides are understood to mean N-acylsphingosine (fatty acid amides of sphingosine) or synthetic analogues of such lipids (so-called pseudo-ceramides)), propellants such as propane-butane mixtures, $N_2O$, dimethyl ether, $CO_2$ and air, antioxidants, preservatives, such as sodium benzoate or salicylic acid, additional viscosity regulators, such as salts (NaCl).

Compositions of the inventive shampoos can have a viscosity ranging from 120,000 cps to 3,000,000 cps. Viscosity can be measured using suitable viscometer known to those of skill in the art. The preferred viscosity range is 1,000,000 cps-2,000,000 cps using a Brookfield RVT Viscometer, Spindle F at 0.5 rpm for 90 sec, with around 1,500,000 cps being the most preferred.

The anhydrous shampoos can be filled and stored in a wide variety of containers. Suitable containers included, but are not limited to, glass or plastic beakers and bottles, tubes, aluminum or plastic jars and tubes, blister packs and other monodose type containers. Suitable plastics include PP, PS, PET, LDPE, HDPE and combinations thereof.

In certain embodiments, the anhydrous compositions can be filled into a container including a fingertip airless pump system. In other embodiments, the compositions can be filled into laminated squeeze tubes. In certain preferred embodiments, the anhydrous shampoo compositions are filled and stored in a monodose container.

Exemplary monodose containers can be standard or customized shapes, which are thermoformed on one or both sides. Monodose containers can be supplied in strip, single with straight cutting or single with outline cutting configurations, with different opening systems (e.g., with pre-cut, without pre-cut, peelable).

The compositions are not limited by the type of container but are advantageous in that they are able to utilize a wider variety of packaging than traditional and bar shampoo products.

The anhydrous shampoo compositions of the invention are used as follows. The product is applied to hair that has been wetted or which will be subsequently wetted. The user will distribute the product throughout the hair mechanically in the usual way of spreading creams and lotions, by rubbing the product with his/her hands or combing through the hair. The compositions, when applied to wetted hair, will foam. The user will massage the hair and scalp, and then the hair is rinsed with water to remove dirt, oils and the majority of the compositions from the hair.

Since the amount of hair on each consumer varies greatly and is user dependent, the amount of anhydrous shampoo product to use is also consumer dependent. However, it is noted that there is no "mixing" needed prior to application to hair; the product is directly applied to wet hair. In testing, the inventors have found that it generally takes half the amount of the anhydrous or substantially anhydrous cream shampoo as described herein to create the same amount of lather/foam compared to a bar shampoo, and a quarter the amount of the anhydrous or substantially anhydrous compositions described herein as compared to a traditional shampoo.

Accordingly, the anhydrous and substantially anhydrous shampoos described herein will create the same foaming properties upon application to wet hair as compared to twice as much of a bar shampoo. The anhydrous and substantially anhydrous shampoos described herein will create the same foaming properties upon application to wet hair as compared to four times as much of a traditional water-based shampoo that is not anhydrous or substantially anhydrous.

The present invention achieves an anhydrous foamable composition without using oils or detergents. Specifically, the present invention achieves a high foaming structured cream by combining propanediol and the two surfactants, SCI, and SLMI or SCMI. As such, the anhydrous composition disclosed in the present invention is more suitable for hair care, as it achieves the desired foaming consistency without use of oils and harsh detergents. Furthermore, glycerin and propanediol solubilize while other cosmetic solubilizers will separate and/or don't foam.

The present invention achieves a high foaming anhydrous foamable composition that will be acceptable to consumers by incorporating propanediol, and desirably also glycerin, both of which are naturally conditioning of keratin, this leaving hair both clean and conditioned.

Accordingly, the present invention provides anhydrous hair care shampoos which foam very well, clean the hair excellently, are well tolerated by the skin, and give the hair further improved care properties, in particular more shine, softness and volume.

EXAMPLES

Example 1—Surfactant Solubilization

The solubility of 10% SCI and 0-10% SLMI was observed in various solvents and diluents.

| Sample | Solvent/Diluent | % w/w | SCI () % | SLMI % | Observation |
|---|---|---|---|---|---|
| A | Water | 90 | 10 | 0 | Partial solubility at 25 C. Full solubility when heated to 80-85 C. Water thin liquid. |
| B | Glycerin | 90 | 10 | 0 | No solubility at 25 C. Full solubility at 80-85 C. but takes a long time. Viscous liquid when cooled to 25 C. |
| C | Propanediol | 90 | 10 | 0 | No solubility at 25 C. Full solubility at 80-85 C. Mixture separates when cooled to 25 C. Water thin liquid. |
| D | Glycerin Propanediol | 45 45 | 10 | 0 | No solubility at 25 C. Full solubility at 80-85 C. for a shorter mixing time than sample B&C. Less viscous than sample B. |
| E | Glycerin | 80 | 10 | 10 | No solubility at 25 C. and partial solubility at 80-85 C. Viscous when cooled to 25 C. with particles SLMI) at bottom. |
| F | Propanediol | 80 | 10 | 10 | No solubility at 25 C. and full solubility at 80-85 C. Viscous/creamy when cooled to 25 C. |
| G | Sunflower Oil | 80 | 10 | 0 | No solubility at 25 C. and 80-85 C. |

Example 2—Surfactant Solubilization

The solubility of 10% SCI and 10% SLMI (1:1) was observed in various solvents and diluents:

| Sample | Emollient | % w/w | SCI % | SLMI % | Observation |
|---|---|---|---|---|---|
| A | Glycerin | 80 | 10 | 10 | Form viscous gel-like cream. Medium foaming. |
| B | Propanediol | 80 | 10 | 10 | Form viscous opaque cream. High foaming. |
| C | Propylene Glycol | 80 | 10 | 10 | Thin liquid that separates. Surfactant solution at bottom and propylene glycol at top. Medium foaming (when mixed). |
| D | Mineral Oil | 80 | 10 | 10 | SLMI is partially solubilized. Thin liquid with separation, creamy white liquid (surfactant) at bottom and clear liquid at top (mineral oil). Light foaming. |
| E | Caprylic/Capric Triglyceride | 80 | 10 | 10 | Semi-viscous liquid. No foaming, oily residue. |
| F | Isododecane | 80 | 10 | 10 | Semi-viscous liquid. No foaming, oily residue |
| G | Ethylhexyl Palmitate | 80 | 10 | 10 | SLMI is partially solubilized. Thin liquid with separation. Light foaming (when mixed). |

-continued

| Sample | Emollient | % w/w | SCI % | SLMI % | Observation |
|---|---|---|---|---|---|
| H | Isopropyl Myristate | 80 | 10 | 10 | SLMI is partially solubilized. Thin liquid with separation. Little to no foaming (when mixed). |

Example 3—Surfactant Solubilization

The solubility of 20% SLMI was observed in various solvents and diluents.

| Sample | Solvent/ Diluent | % w/w | SLMI % | Observation |
|---|---|---|---|---|
| A | Water | 80 | 20 | Partial solubility at 25 C. Soluble at 80-85 C. Separates with white precipitate (surfactant) at bottom and water at top when cooled. |
| B | Glycerin | 80 | 20 | No solubility at 25 C. Mostly soluble at 80-85 C., viscous solution with a few particles when cooled to 25 C. |
| C | Propanediol | 80 | 20 | Partial solubility at 80-85 C. No solubility at 25 C. Thin liquid with particles at bottom and separation with clear and cloudy layer. |
| D | Glycerin Propanediol | 40 40 | 20 | No solubility at 25 C. Partial solubility at 80-85 C. Separation with viscous/creamy phase at top and clear liquidat bottom. |
| E | Mineral Oil | 80 | 20 | No solubility at 25 C. and 80-85 C. |

Example 4—Anhydrous Shampoo Composition

A formulation of an anhydrous cream shampoo composition in accordance with the invention was developed.

| Ingredient (INCI) | Alternative Ingredient (INCI) | Function | % w/w |
|---|---|---|---|
| Glycerin | N/A | Solubilizer/ Conditioning Agent | 25-50 |
| Guar Hydroxypropyltrimonium Chloride | Hydroxypropyl Guar Hydroxypropyl Guar Hydroxypropyltrimonium Chloride | Binder/Film Former | 0.2-0.4 |
| Citric acid | N/A | pH adjuster | 0.17-0.2 |
| Propanediol | N/A | Solubilizer/ Conditioning Agent/Foam Booster/ Preservative Booster | 25-50 |
| Sodium Lauroyl Methyl Isethionate | Sodium Cocoyl Methyl Isethionate | Surfactant | 10.5-20 |
| *Raphanus Sativus* (Raddish) Seed Extract | *Cocos Nucifera* (Coconut) Oil *Melianthus Annuus* (Sunflower) Seed Oil *Limnanthes Alba* (Meadowfoam) Seed Oil | Conditioning Agent | 0-2.0 |
| Sodium Cocoyl Isethionate | N/A | Surfactant | 12.5-25 |
| Fragrance/Parfum | N/A | Fragrance | 0-0.5 |

Example 5—Methods of Manufacture

Methods of manufacture of anhydrous shampoo compositions in accordance with the invention were developed and are disclosed below.

Method 1: To a suitable tank equipped with turbine and sweep mixing and a heating and cooling jacket add glycerin and begin mixing with medium agitation. Begin heating to 70-85° C. and add propanediol. When batch is 70-75° C., add SLMI and mix until melted and uniform. Continue heating to 80-85° C. and add SCI. When uniform, add any other ingredients while cooling to 40-45° C. and mix for min 30 minutes or until uniform.

Method 2: To a suitable tank equipped with turbine and sweep mixing and a heating and cooling jacket add glycerin and begin mixing with medium agitation. Add any guar polymers and mix until uniformly dispersed. Begin heating to 80-85° C. and add citric acid, propanediol, while heating. Mix uniformly. When batch is 70-75° C., add SLMI and mix until melted and uniform. Slowly add any chelating agent and mix until uniform. Continue heating to 80-85° C. and add SCI. Cool to 40-45° C. Add any emollient wax when batch is at 60-65° C. and mix until uniform. Add cosmetic oil(s) and mix until uniform. When batch reaches 40-45° C., add any preservatives, antioxidants, fragrance and mix until uniform. Mix for min 30 minutes or until uniform.

Method 3: To a suitable tank equipped with turbine and sweep mixing and a heating and cooling jacket add glycerin and begin mixing with medium agitation. Add any guar polymers and mix until uniformly dispersed. Begin heating to 70-75° C. and add citric acid, propanediol, and any sodium benzoate while heating. Mix uniformly. When batch is 70-75° C., add SLMI and mix until melted and uniform. Slowly add any chelating agent and mix until uniform. Cool to 40-45° C. Add any emollient wax when batch is at 60-65° C. and mix until uniform. Add any cosmetic oil(s) and SCI and mix until uniform. When batch reaches 40-45° C., add any antioxidants, fragrance and mix until uniform. QS to desired amount and mix for min 30 minutes or until uniform.

Method 4: To a suitable tank equipped with turbine and sweep mixing and a heating and cooling jacket add glycerin and begin mixing with medium agitation. Add any guar polymers and mix until uniformly dispersed. Begin heating to 70-75° C. and add citric acid. When batch is 70-75° C., add SLMI and mix until melted and uniform. Add any chelating agent and mix until uniform. In a separate vessel equipped with variable speed mixing, add Propanediol while heating to 70-75° C. Add SCI and mix until uniform. When uniform, add to other ingredients and mix until uniform, Cool to 40-45° C. Add any preservative and fragrance. QS to desired amount and mix for min 30 minutes or until uniform.

The shampoos manufactured according to methods 1-4 are filled and stored in various containers, selected from glass or plastic beaker, bottles, tubes, aluminum or plastic jars, blister packs and other monodose type containers.

Example 6 Viscosity

The viscosity of various combinations of propanediol, SCI and SLMI was measured using a Brookfield RVT Viscometer, Spindle F.

| Sample | Propanediol % | SCI % | SLMI % | Spindle Setting | Viscosity (cps) |
|---|---|---|---|---|---|
| A | 80 | 10 | 10 | RV-T-F @ 2.5 rmp @60 sec | 544,000 |
| B | 75 | 10 | 15 | RV-T-F @ 2.5 rmp @ 60 sec | 1,200,000 |
| C | 70 | 10 | 20 | RV-T-F @ 0.5 rmp @ 90 sec | 3,000,000 |
| D | 75 | 15 | 10 | RV-T-F @ 2.5 rmp @ 60 sec | 280,000 |
| E | 70 | 20 | 10 | RV-T-F @ 2.5 rmp @ 60 sec | 120,000 |

Example 7—Butter Shampoos (Water-Free)

A formulation of an anhydrous butter shampoo composition in accordance with the invention was developed.

| Ingredient | A | B | C | D | E |
|---|---|---|---|---|---|
| | Weight (g) | | | | |
| Glycerin | 273.15 | 251.15 | 273.15 | 251.15 | 628.50 |
| Guar Hydroxypropyltrimonium Chloride | 1.00 | 1.00 | 1.00 | 1.00 | 3.00 |
| Citric acid | 0.85 | 0.85 | 0.85 | 0.85 | 3.00 |
| Propanediol | 40.00 | 75.00 | 40.00 | 75.00 | 375.00 |
| Sodium benzoate | 2.50 | — | 2.50 | — | — |
| SLMI | 87.50 | 87.50 | 87.50 | 87.50 | 225.00 |
| Trisodium Ethylenediamine Disuccinate | 7.50 | 7.50 | 7.50 | 7.50 | — |
| *Cocos Nucifera* (Coconut) Oil | 10.00 | — | 10.00 | — | — |
| *Raphanus Sativus* (Raddish) Seed Extract | 10.00 | — | 10.00 | 10.00 | 30.00 |
| SCI | 62.50 | 62.50 | 62.50 | 62.50 | 225.00 |
| Vitamin E-Acetate | — | — | 2.50 | — | — |
| Fragrance/Parfum | — | — | 2.50 | 2.50 | 3.00 |
| Benzyl Alcohol | — | 2.50 | — | 2.50 | 7.50 |

Having described the invention with reference to a particular composition and the like, it will be apparent to those of skill in the art that it is not intended that the invention be limited by such embodiments, and that modifications can be made without departing from the scope of the invention.

What is claimed is:

1. An anhydrous shampoo composition comprising:
propanediol; and
a single surfactant composition consisting of anionic surfactant, the anionic surfactant including two or more surfactants selected from (a) sodium cocoyl isethionate, and (b) at least one of sodium lauroyl methyl isethionate and sodium cocoyl methyl isethionate;
wherein the shampoo has a viscosity of 120,000 cps-3,000,000 cps.

2. The shampoo composition of claim 1, wherein the composition comprises 25-50% w/w propanediol.

3. The shampoo composition of claim 1, wherein the composition comprises 30-50% w/w propanediol.

4. The shampoo composition of claim 1, wherein the composition comprises 10-45% w/w of the surfactant composition.

5. The shampoo composition of claim 1, wherein the composition comprises 10-25% w/w of the surfactant composition.

6. The shampoo composition of claim 1, wherein the composition comprises 20-45% w/w of the surfactant composition.

7. The shampoo composition of claim 1, wherein the ratio of (a) to (b) is about 1:1.

8. The shampoo composition of claim 1, wherein the ratio of the single surfactant composition to propanediol is about 1.2:1.

9. The shampoo composition of claim 1, wherein the composition further comprises glycerin.

10. The shampoo composition of claim 9, wherein the composition comprises 30-50% w/w of glycerin.

11. The shampoo composition of claim 10, further comprising about 0.2% w/w citric acid.

12. The shampoo composition of claim 1, wherein the shampoo is a cream.

13. The shampoo composition of claim 1, having a viscosity of 1,000,000 cps-2,000,000 cps.

14. The anhydrous shampoo composition of claim 1, further comprising at least one of fragrance, conditioning agent, preservative, gums, buffering agent, and emollient.

15. A cleaning composition comprising:
30-50% w/w propanediol; and
10-45% w/w of a surfactant composition consisting of anionic surfactant, the anionic surfactant including two or more surfactants selected from (a) sodium cocoyl isethionate and (b) at least one of one of sodium lauroyl methyl isethionate and sodium cocoyl methyl isethionate,
wherein no additional surfactants are present,
wherein the composition has a viscosity of 120,000 cps-3,000,000 cps and is substantially free of water.

16. The cleaning composition of claim 15, wherein the anionic surfactants are selected from sodium cocoyl isethionate and sodium lauroyl methyl isethionate.

17. The composition of claim 15, further comprising glycerin.

18. The composition of claim 17, wherein the composition comprises 30-50% w/w of glycerin.

19. A cleaning composition consisting essentially of:
25-50% w/w propanediol;
10-25% w/w sodium cocoyl isethionate;
10-20% w/w at least one of one of sodium lauroyl methyl isethionate and sodium cocoyl methyl isethionate;
25-50% w/w glycerin;
0-0.5% w/w cationic guar polymer;
0-2.0% w/w conditioning agent; and
0-0.5% w/w fragrance,
wherein no additional surfactants are present
wherein the composition has a viscosity of 1,000,000 cps to 2,000,000 cps and is free of added water.

20. The cleaning composition of claim 15, further comprising 0.2-0.4% w/w guar polymer and about 0.17-0.2% w/w citric acid.

* * * * *